United States Patent
Sako

(10) Patent No.: US 8,374,814 B2
(45) Date of Patent: Feb. 12, 2013

(54) X-RAY DETECTION SIGNAL PROCESSING APPARATUS AND METHOD THEREFOR

(75) Inventor: Yukio Sako, Takatsuki (JP)

(73) Assignee: Rigaku Corporation, Tokyo (JP)

( * ) Notice: Subject to any disclaimer, the term of this patent is extended or adjusted under 35 U.S.C. 154(b) by 0 days.

(21) Appl. No.: 13/499,581

(22) PCT Filed: Oct. 26, 2011

(86) PCT No.: PCT/JP2011/074634
§ 371 (c)(1),
(2), (4) Date: Mar. 30, 2010

(87) PCT Pub. No.: WO2012/111195
PCT Pub. Date: Aug. 23, 2012

(65) Prior Publication Data
US 2012/0207277 A1    Aug. 16, 2012

(30) Foreign Application Priority Data
Feb. 16, 2011  (JP) .................. 2011-031141

(51) Int. Cl.
*G01R 23/02* (2006.01)
*G01R 29/027* (2006.01)
*H05G 1/64* (2006.01)
(52) U.S. Cl. ............... 702/79; 702/78; 378/98.9
(58) Field of Classification Search .......... 378/98.9; 702/78, 79
See application file for complete search history.

(56) References Cited

U.S. PATENT DOCUMENTS

| | | | | |
|---|---|---|---|---|
| 5,532,944 A | * | 7/1996 | Battista | 708/3 |
| 5,774,522 A | | 6/1998 | Warburton | |
| 7,855,370 B2 | * | 12/2010 | Mott | 250/370.06 |
| 7,966,155 B2 | * | 6/2011 | Warburton et al. | 702/190 |
| 2003/0040877 A1 | * | 2/2003 | Warburton et al. | 702/78 |

FOREIGN PATENT DOCUMENTS

| | | |
|---|---|---|
| JP | 7-79143 A | 3/1995 |
| JP | 2008-002920 A | 1/2008 |
| JP | 4083802 B2 | 4/2008 |
| JP | 2009-229127 A | 10/2009 |

OTHER PUBLICATIONS

Y. Koshi et al., "Enerugi Bunsan-gata Ekkusu-sen Bunseki: Handoutai Kenshutsuki-no Tsukaikata (Energy Dispersive X-ray Analysis: How to Use the Semiconductor Detector)" Spectroscopical Society of Japan Measurement Method Series, Jun. 30, 1989, pp. 30-33, No. 18.

Helmuth Spieler et al., "Semiconductor Detector Systems", Series on Semiconductor Science and Technology, 2009, pp. 175-179, No. 12.

* cited by examiner

*Primary Examiner* — Thomas R Artman
(74) *Attorney, Agent, or Firm* — Sughrue Mion, PLLC

(57) ABSTRACT

An X-ray detection signal processing apparatus of the present invention is such that after a signal from a preamplifier has been converted into a digital signal at a high speed by means of a high speed analog-to-digital converter (1), a process for removing influences brought about by a component that has been decayed by a differential time constant in the preamplifier is performed on a digital basis in a digital signal processing block (2). An event detecting unit (3) within the digital signal processing block (2), smoothen the signal from the high speed analog-to-digital converter (1) for a predetermined shaping time with the use of a filter function for high speed shaping, detects as an event information the timing at which the smoothened signal exceeds a predetermined threshold and attains the maximum value, and add such event information to the signal from the high speed analog-to-digital converter (1).

3 Claims, 1 Drawing Sheet

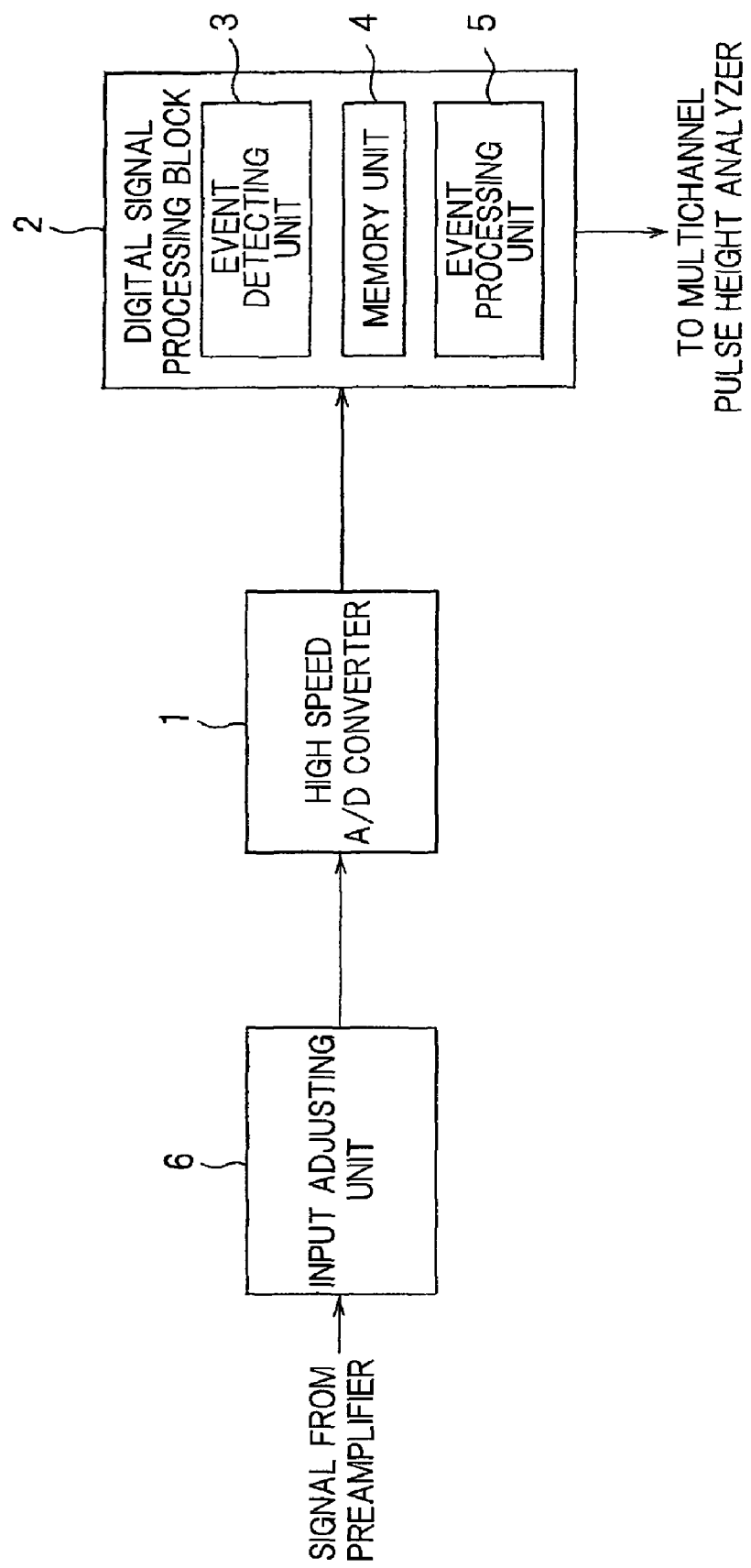

X-RAY DETECTION SIGNAL PROCESSING APPARATUS AND METHOD THEREFOR

CROSS REFERENCE TO THE RELATED APPLICATION

This application is based on and claims Convention priority to Japanese patent application No. 2011-031141, filed Feb. 16, 2011, the entire disclosure of which is herein incorporated by reference as a part of this application.

BACKGROUND OF THE INVENTION

1. Field of the Invention

The present invention relates to an X-ray detection signal processing apparatus for and a method of receiving a signal, which has been generated from an X-ray detector and has subsequently been passed through a preamplifier, to output a signal of a pulse height proportional to an energy of X-rays incident on the X-ray detector.

2. Description of Related Art

In the X-ray fluorescence analysis, for example, a signal generated from an X-ray detector has hitherto been differentiated by a preamplifier of a pulse reset type or a register feedback type for the purpose of removing a direct current component and, accordingly, it contains a component that is decayed by a differential time constant. If such an analog signal in the form as presented is converted into a digital signal and is then supplied to a pulse height analyzer, the gain and the base line tend to change and, therefore, conversion into the digital signal has carried after a treatment, in the analog signal processing apparatus, had been effected to remove influences that might be brought about by the component tending to be decayed by the differential time constant, and is then supplied to the pulse height analyzer. In this connection, see, for example, the non-patent documents 1 and 2 listed below. In this instance, the influences brought about by the component tending to be decayed by the differential time constant includes a change in final gain, that results from a change of a convergence value of a signal tending to be decayed by the differential time constant, and a change in final base line that results from a change of the differential time constant itself. Also, the digital signal processing apparatus in which a treatment similar to that discussed above is carried out on a digital basis.

In this connection, see the patent document 1 listed below.

[Prior Art Literature]

[Patent Document 1] JP Patent No. 4083802

[non-Patent Document 1] Y. Koshi and K. Sato, "Enerugi Bunsan-gata Ekkusu-sen Bunseki: Handoutai Kenshutsukino Tsukaikata (Energy Dispersive X-ray Analysis: How to Use the Semiconductor Detector)", Nippon Bunko Gakkai Sokuteihou Sirizu No. 18 (Spectroscopical Society of Japan Measurement Method Series No. 18), first edition, Kabushiki Kaisha Gakkai Shuppan Senta, Jun. 30, 1989, pp. 30-33.

[non-Patent Document 2] Helmuth Spieler, "Semiconductor Detector Systems", Series on Semiconductor Science and Technology No. 12, Oxford University Press Inc., 2009, pp. 175-179.

It has, however, been found that the analog signal processing apparatus of the kind referred to above tends to become complicated in structure, requiring several hundred component parts and, also, requires a complicated adjustment. On the other hand, the digital signal processing apparatus of the kind referred to above, although simple in structure, is incapable of sufficiently removing the change in the final base line resulting from the change of the differential time constant itself.

SUMMARY OF THE INVENTION

The present invention herein disclosed has been devised to substantially eliminate the problems and inconveniences inherent in the prior art signal processing apparatuses of the kind discussed hereinabove and is intended to provide a X-ray detection signal processing apparatus, which is simplified in structure and adjustment and which is capable of outputting a signal of a high S/N ratio having a pulse height accurately proportional to an energy of X-rays incident on an X-ray detector.

Another important object of the present invention is to provide a method that is executed in the X-ray detection processing apparatus of the type referred to above.

In order to accomplish these objects of the present invention, the present in accordance with a first aspect thereof provides an X-ray detection signal processing apparatus for receiving a signal, which has been generated from an X-ray detector and has subsequently been passed through a preamplifier, to output a signal of a pulse height proportional to an energy of X-rays incident on the X-ray detector, which apparatus includes a high speed analog-to-digital converter for converting the signal from the preamplifier into a digital signal, and a digital signal processing block for processing the digital signal from the high speed analog-to-digital converter. And, the digital signal processing block includes an event detecting unit which is operable to smoothen the signal from the high speed analog-to-digital converter for a predetermined shaping time with the use of a filter function for high speed shaping, then to detect as event information the timing at which a signal so smoothened attains a maximum value in excess of a predetermined threshold and finally to add the event information to the signal from the high speed analog-to-digital converter, a memory unit for sequentially storing a signal from the event detecting unit, and an event processing unit.

The event processing unit referred to above is operable to initiate, when receiving from the event detecting unit the signal added with the event information, an event processing in response to an event accession so that the signal from the event detecting unit and a signal read out sequentially backwardly from the memory unit can be smoothened for the predetermined shaping time on the basis of a convergence value of the signal from the event detecting unit and the signal read out sequentially backwardly from the memory unit, a coefficient of decaying waveform correction for counterbalancing the amount of the signal from the event detecting unit, which is decayed by a differential time constant of the preamplifier, and a coefficient of growing waveform correction for counterbalancing the amount of the signal read out sequentially backwardly from the memory unit, which is increased by the differential time constant of the preamplifier, and the smoothened signal from the event detecting unit, from which the smoothened signal read out sequentially backwardly from the memory unit has been subtracted, can be determined as a signal relative to an event, and to terminate the event processing in response to the event accession.

Further, the event processing unit is operable when the event processing in response to the event accession has been terminated, to continue a process, similar to the event processing in response to the event accession, up until it receives a signal fed from the event detecting unit and added with a subsequent event information, so that the convergence value of the signal from the event detecting unit and the signal read out sequentially backwardly from the memory unit can be determined on the basis of neighboring smoothened signals from the event detecting unit and a gradient obtained from the difference between those neighboring smoothened signals and, also, on the basis of the smoothened signal from the event detecting unit, from which the smoothened signal read out sequentially backwardly from the memory unit has been subtracted, an energy zero value, which is an output value when no X-rays are incident on the X-ray detector, can be determined, and then to output the signal relative to the event from which the energy zero value has been subtracted, as the signal of the pulse height proportional to the energy of the X-rays incident on the X-ray detector.

With the X-ray detection signal processing apparatus of the structure designed in accordance with the first aspect of the present invention described above, the signal from the preamplifier is, after having been converted into the digital signal by means of the high speed analog-to-digital converter, processed to remove influences brought about by a component that is decayed by the differential time constant on a digital basis in the digital signal processing block. Since the digital signal processing block is comprised of an FPGA (Field-Programmable Gate Array) and firmware or a DSP (Digital Signal Processor) and a program, according to the X-ray detection signal processing apparatus designed in accordance with the first aspect of the present invention, the signal of the pulse height accurately proportional to the energy of the X-rays incident on the X-ray detector and having a high S/N ratio can be outputted with a simplified construction and adjustment. The X-ray detection signal processing apparatus designed in accordance with the first aspect of the present invention is preferably provided with an input adjusting unit for adjusting the level of the signal from the preamplifier so as to fall within an input range of the high speed analog-to-digital converter.

The present invention in accordance with a second aspect thereof provides an X-ray detection signal processing method, which includes using the X-ray detection signal processing apparatus designed in accordance with the first aspect of the present invention; processing the signal generated from the X-ray detector and having been passed through the preamplifier; and outputting the signal of the pulse height proportional to the energy of the X-rays incident on the X-ray detector. Even with this X-ray detection signal processing method, functions and effects similar to those afforded by the X-ray detection signal processing apparatus of the present invention can be appreciated.

BRIEF DESCRIPTION OF THE DRAWINGS

In any event, the present invention will become more clearly understood from the following description of preferred embodiments thereof, when taken in conjunction with the accompanying drawings. However, the embodiments and the sole drawing are given only for the purpose of illustration and explanation, and are not to be taken as limiting the scope of the present invention in any way whatsoever, which scope is to be determined by the appended claims:

FIG. 1 is a block diagram showing an X-ray detection signal processing apparatus designed in accordance with a preferred embodiment of the present invention.

DESCRIPTION OF PREFERRED EMBODIMENTS

Hereinafter, reference is made to the sole accompanying drawings for detailed discussion of a preferred embodiment of the present invention. As shown in the sole accompanying drawing, an X-ray detection signal processing apparatus designed according to the present invention is of a type in which a signal, generated from an X-ray detector and subsequently passed through a preamplifier, is inputted and a signal of a pulse height proportional to an energy of X-rays incident on the X-ray detector is outputted. This signal processing apparatus includes a high speed analog-to-digital (A/D) converter 1 for converting an output signal of the preamplifier into a digital signal at a high speed, and a digital signal processing block 2 for processing the digital signal fed from the high speed analog-to-digital converter 2. In this X-ray detection signal processing apparatus, the use is made of an input adjusting unit 6 in the front stage of the high speed analog-to-digital converter 1, which unit 6 is operable to adjust the level of the output signal from the preamplifier within an input range of the high speed analog-to-digital converter 1 and, therefore, the output signal from the preamplifier is supplied to the high speed analog-to-digital converter 1 through the input adjusting unit 6. The level adjustment accomplished by the input adjusting unit 6 may be carried out either by detecting an input voltage supplied to the high speed analog-to-digital converter 1 and giving feedback or by detecting a value after the A/D conversion and giving feedback. Also, the high speed analog-to-digital converter performs a repeated A/D conversion at a predetermined speed, for example, about 40 MHz which is enough to detect a step change caused by an event accession as will be discussed later.

The digital signal processing block 2 includes an event detecting unit 3, a memory unit 4, and an event processing unit 5. The event detecting unit 3 is operable to smoothen the signal from the high speed analog-to-digital converter 1 for a predetermined shaping time with the use of a filter function for high speed shaping, then to detect as event information the timing at which a signal so smoothened attains a maximum value in excess of a predetermined threshold and finally to add the event information to the signal from the high speed analog-to-digital converter 1. The memory unit 4 is operable to sequentially store a signal from the event detecting unit 3.

The event processing unit 5, when receiving from the event detecting unit 3 the signal added with the event information, initiates an event processing in response to an event accession so that the signal from the event detecting unit 3 and a signal read out sequentially backwardly from the memory unit 4 can be smoothened for the predetermined shaping time on the basis of a convergence value of the signal from the event detecting unit and the signal read out sequentially backwardly from the memory unit, a coefficient of decaying waveform correction for counterbalancing the amount of the signal from the event detecting unit 3, which is decayed by a differential time constant of the preamplifier, and a coefficient of growing waveform correction for counterbalancing the amount of the signal read out sequentially backwardly from the memory unit 4, which is increased by the differential time constant of the preamplifier, and the smoothened signal from the event detecting unit 3, from which the smoothened signal read out sequentially backwardly from the memory unit 4 has been subtracted, can be determined as a signal relative to an event before the event processing in response to the event accession is terminated.

Also, the event processing unit 5, when the event processing in response to the event accession has been terminated, continues a process, similar to the event processing in response to the event accession, up until it receives a signal fed from the event detecting unit 3 and added with a subsequent event information, so that the convergence value of the signal from the event detecting unit 3 and the signal read out sequentially backwardly from the memory unit 4 can be determined on the basis of neighboring smoothened signals from the event detecting unit 3 and a gradient obtained from the difference between those neighboring smoothened signals and, also, on the basis of the smoothened signal from the event detecting unit 3, from which the smoothened signal read out sequentially backwardly from the memory unit 4 has been subtracted, an energy zero value, which is an output value when no X-rays are incident on the X-ray detector, can be determined, and then outputs the signal relative to the event from which the energy zero value has been subtracted, as the signal of the pulse height proportional to the energy of the X-rays incident on the X-ray detector.

The operation of the digital signal processing block 2 will be described hereinafter, using and with reference to mathematical expressions. The signal from the analog-to-digital converter is outputted from the last stage as a signal Ui after having passed through a multi-stage shift register in the event detecting unit 3 of the digital signal processing block 2. On the other hand, with respect to a signal Ai from each stage of the shift register, by the following expression (1), a smoothing process is carried out and the event accession, that is, arrival of the X-ray detection signal is detected.

In the expression (1) above, the parameter F represents a smoothened signal obtained by shaping the input signal Ai for a predetermined shaping time (about several ten nanoseconds) at a high speed, the parameter Cn represents a filter function for a high speed shaping. The event detecting unit 3 detects as event information the timing at which the smoothened signal F has exceeded a predetermined threshold d and then attained the maximum value and, also, adds the detected event information to the signal from the high speed analog-to-digital converter 1, that is, to adds the detected event information to the previously described signal Ui, and then outputs it.

The signal Ui from the event detecting unit 3 is successively stored in the memory unit 4 and the write-in address grows m to m+1. At this time, if the event information is added to the signal Ui, that is, the event information contained in the signal Ui is true, the event processing in response to the event accession as will be described later is triggered in the event processing unit 5. Once the event processing in response to the event accession terminates, a similar event proceeding is successively triggered until the signal Ui added with the subsequent event information arrives, thus performing a Get_Zero process as will be described later.

The event processing unit 5, upon receipt from the event detecting unit 3 the signal Ui which has been added with the event information, initiates the event processing in response to the event accession, and, by the following expressions (2) and (3), smoothens the signal Ui from the event detecting unit 3 and a signal Vi read out sequentially backwardly from the memory unit 4 (the read-out address changes step by step from m−1, then m−2, m−3, and so on) for the predetermined shaping time on the basis of a convergence value P_Zero of the signal Ui from the event detecting unit 3 and the signal Vi read out sequentially backwardly from the memory unit 4, an decaying waveform correction coefficient Fi, required for the signal Ui from the event detecting unit 3 to counterbalance the amount decayed in the preamplifier by the differential time constant, and an increasing waveform correction coefficient Gi, required for the signal Vi read out sequentially successively from the memory unit 4 to counterbalance the amount increased in the preamplifier by the differential time constant.

$$SA = \frac{\sum_{i=1}^{l}(U_i - \text{P\_Zero})Fi}{l} \quad (2)$$

$$SB = \frac{\sum_{i=1}^{l}(V_i - \text{P\_Zero})Gi}{l} \quad (3)$$

In those expressions (2) and (3), each of the decaying waveform correction coefficient Fi and the increasing waveform correction coefficient Gi is a function of the differential time constant Tto in the preamplifier and the interval (dependent on the previously described predetermined shaping time) of data that sent to the event processing unit 5 and is represented by an exponential function, and the decaying waveform correction coefficient Fi and the increasing waveform correction coefficient Gi become an increasing function and a decreasing function, respectively, and those can be calculated beforehand. In addition, those exponential functions, when multiplied by a function (for example, a trapezoidal waveform or a Gaussian waveform) that is generally utilized for smoothening, can provide a correction coefficient having an excellent S/N ratio.

Subsequently, the smoothened signal SA from the event detecting unit 3, from which the smoothened signal SB read out sequentially backwardly from the memory unit 4 is subtracted, is determined as the signal SE relative to the event from the following expression (4), thus terminating the event processing in response to the event accession.

$$SE = SA - SB \quad (4)$$

It is to be noted that the event processing unit 5 outputs, at the final stage, the signal SEo, which corresponds to the signal SE relative to the event from which an energy zero value B_Zero, as will be described, is subtracted, according to the following expression (5), as the signal SEo of the pulse height proportional to the energy of the X-rays incident on the X-ray detector.

$$SEo = SE - B\_Zero \quad (5)$$

Upon termination of the event processing in response to the event accession, the event processing unit 5 performs the Get_Zero process until it receives from the event detecting unit 3 the signal added with the subsequent event information, by repeating the process similar to the event processing in response to the event accession. More specifically, by obtaining the value Zp after the passage of the differential time constant Tto from the following expression (6) on the basis of neighboring smoothened signals SAb and SAa from the event detecting unit 3 and the gradient obtained from the difference therebetween and by performing the smoothening (for example, exponentially smoothening) process, the convergence value P_Zero of the signal Ui from the event detecting unit 3 and the signal Vi read out sequentially backwardly from the memory unit 4 is determined.

$$Zp = (SAb + SAa)/2 - Tto(SAb - SAa)/g + P\_Zero \quad (6)$$

Also, from the expression (7) below, by obtaining the signal Zb, which corresponds to the smoothened signal SA from the event detecting unit 3 from which the smoothened signal SB read out sequentially backwardly from the memory unit 4 has been subtracted and by performing the smoothening (for example, exponentially smoothening) process, the energy zero value B_Zero, which is an output value when no X-ray is incident on the X-ray detector, is determined.

$$Zb = SA - SB \quad (7)$$

As hereinabove described, in the X-ray detection signal processing apparatus according to the foregoing embodiment of the present invention, the signal from the preamplifier is, after having been converted from the analog signal to the digital signal at a high speed with the use of the high speed analog-to-digital converter 1, subjected to the process performed in the digital signal processing block 2 on a digital basis to remove the influences brought about by the component decayed by the differential time constant. Since the digital signal processing block 2 can be constructed with an FPGA and firmware or DSP and a program, according to the X-ray detection signal processing apparatus according to the embodiment of the present invention, the signal of the pulse height accurately proportional to the energy of the X-rays incident on the X-ray detector and having a high S/N ratio can be outputted with a simplified construction and adjustment. Also, the FPGA forming the digital signal processing block 2 can have a multichannel pulse height analyzer built therein.

It is to be noted that the present invention should be equally construed as including an X-ray detection signal processing method in which by operating the X-ray detection signal processing apparatus according to the embodiment of the present invention in the manner described above, the signal generated from the X-ray detector and having been passed through the preamplifier is processed and the signal of the pulse height proportional to the energy of the X-rays incident on the X-ray detector is then outputted. Even with this X-ray detection signal processing method, functions and effects similar to those afforded by the X-ray detection signal processing apparatus of the present invention can be appreciated.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

[Reference Numerals]
  1 . . . High speed analog-to-digital converter
  2 . . . Digital signal processing block
  3 . . . Event detecting unit
  4 . . . Memory unit
  5 . . . Event processing unit
  6 . . . Input adjusting unit

What is claimed is:

1. An X-ray detection signal processing apparatus for receiving a signal, which has been generated from an X-ray detector and has subsequently been passed through a preamplifier, to output a signal of a pulse height proportional to an energy of X-rays incident on the X-ray detector, which apparatus comprises:
   a high speed analog-to-digital converter for converting the signal from the preamplifier into a digital signal; and
   a digital signal processing block for processing the digital signal from the high speed analog-to-digital converter, the digital signal processing block comprising:
      an event detecting unit which is operable to smoothen the signal from the high speed analog-to-digital converter for a predetermined shaping time with the use of a filter function for high speed shaping, then to detect as event information the timing at which a signal so smoothened attains a maximum value in excess of a predetermined threshold and finally to add the event information to the signal from the high speed analog-to-digital converter;
      a memory unit for sequentially storing a signal from the event detecting unit;
      an event processing unit;
   wherein the event processing unit is operable to initiate, when receiving from the event detecting unit the signal added with the event information, an event processing in response to an event accession so that the signal from the event detecting unit and a signal read out sequentially backwardly from the memory unit can be smoothened for the predetermined shaping time on the basis of a convergence value of the signal from the event detecting unit and the signal read out sequentially backwardly from the memory unit, a coefficient of decaying waveform correction for counterbalancing the amount of the signal from the event detecting unit, which is decayed by a differential time constant of the preamplifier, and a coefficient of growing waveform correction for counterbalancing the amount of the signal read out sequentially backwardly from the memory unit, which is increased by the differential time constant of the preamplifier, and the smoothened signal from the event detecting unit, from which the smoothened signal read out sequentially backwardly from the memory unit has been subtracted, can be determined as a signal relative to an event, and to terminate the event processing in response to the event accession;
      when the event processing in response to the event accession has been terminated, to continue a process, similar to the event processing in response to the event accession, up until it receives a signal fed from the event detecting unit and added with a subsequent event information, so that the convergence value of the signal from the event detecting unit and the signal read out sequentially backwardly from the memory unit can be determined on the basis of neighboring smoothened signals from the event detecting unit and a gradient obtained from the difference between those neighboring smoothened signals and, also, on the basis of the smoothened signal from the event detecting unit, from which the smoothened signal read out sequentially backwardly from the memory unit has been subtracted, an energy zero value, which is an output value when no X-rays are incident on the X-ray detector, can be determined, and then to output the signal relative to the event from which the energy zero value has been subtracted, as the signal of the pulse height proportional to the energy of the X-rays incident on the X-ray detector.

2. The X-ray detection signal processing apparatus as claimed in claim 1, further comprising an input adjusting unit for adjusting the level of the signal from the preamplifier so as to fall within an input range of the high speed analog-to-digital converter.

3. An X-ray detection signal processing method which comprises:
   using the X-ray detection signal processing apparatus as defined in claim 1;
   processing the signal generated from the X-ray detector and having been passed through the preamplifier; and
   outputting the signal of the pulse height proportional to the energy of the X-rays incident on the X-ray detector.

* * * * *

UNITED STATES PATENT AND TRADEMARK OFFICE
CERTIFICATE OF CORRECTION

| | | |
|---|---|---|
| PATENT NO. | : 8,374,814 B2 | Page 1 of 1 |
| APPLICATION NO. | : 13/499581 | |
| DATED | : February 12, 2013 | |
| INVENTOR(S) | : Yukio Sako | |

It is certified that error appears in the above-identified patent and that said Letters Patent is hereby corrected as shown below:

In the Specification

Column 5, line 25: Insert the equation as follows $$F = \frac{\sum_{n=1}^{l} C_n (A_{k-n} - A_{k+n})}{\sum_{n=1}^{l} C_n} > d \quad (1)$$

Signed and Sealed this
Twenty-fourth Day of February, 2015

Michelle K. Lee
*Deputy Director of the United States Patent and Trademark Office*